(12) United States Patent
Zeidler et al.

(10) Patent No.: US 12,734,688 B2
(45) Date of Patent: Sep. 15, 2026

(54) MOTION CONTROL FOR A MEDICAL INSTALLATION

(71) Applicant: Siemens Healthineers AG, Forchheim (DE)

(72) Inventors: Josef Zeidler, Marktredwitz (DE); Sebastian Boessl, Schlammersdorf (DE); Michael Griener, Kemnath (DE); Markus Scherm, Fichtelberg (DE)

(73) Assignee: Siemens Healthineers AG, Forchheim (DE)

( * ) Notice: Subject to any disclaimer, the term of this patent is extended or adjusted under 35 U.S.C. 154(b) by 502 days.

(21) Appl. No.: 18/190,362

(22) Filed: Mar. 27, 2023

(65) Prior Publication Data

US 2023/0311314 A1 Oct. 5, 2023

(30) Foreign Application Priority Data

Mar. 30, 2022 (EP) .................................... 22165569

(51) Int. Cl.
*B25J 9/16* (2006.01)
*A61B 5/00* (2006.01)
(Continued)

(52) U.S. Cl.
CPC ............. *B25J 9/1633* (2013.01); *A61B 5/704* (2013.01); *A61B 50/24* (2016.02); *B25J 13/088* (2013.01)

(58) Field of Classification Search
CPC ....... B25J 9/1633; B25J 13/088; A61B 5/704; A61B 50/24; A61B 6/0407; A61B 6/4464;
(Continued)

(56) References Cited

U.S. PATENT DOCUMENTS 4,904,152 A * 2/1990 Doi .......................... B25J 9/046 414/730
6,459,926 B1 * 10/2002 Nowlin .................. A61B 34/30 600/102

(Continued)

FOREIGN PATENT DOCUMENTS

CN 111146907 A 5/2020
DE 102007031475 A1 1/2009

(Continued)

OTHER PUBLICATIONS

Madsen, Emil et al. Comprehensive modeling and identification of nonlinear joint dynamics for collaborative industrial robot manipulators: , Control Engineering Practice, Seiten 1-11, am 30. Mai 2020 veröffentlicht 30. Mai 2020.

*Primary Examiner* — Wade Miles
*Assistant Examiner* — James Brian Chin
(74) *Attorney, Agent, or Firm* — Harness, Dickey & Pierce, P.L.C.

(57) ABSTRACT

One or more example embodiments relates to a method for controlling a motion of a component of a medical installation, comprising capturing a first position parameter via a first position sensor, the first position sensor being on the component; capturing a second position parameter via a second position sensor, the second position sensor being on the component; determining, by a control unit, a position spacing for the position sensors based on the first position parameter and the second position parameter; and generating a control signal for a drive unit of the component based on the determined position spacing.

18 Claims, 3 Drawing Sheets

(51) Int. Cl.
*A61B 50/24* (2016.01)
*B25J 13/08* (2006.01)

(58) Field of Classification Search
CPC ......... A61B 6/54; A61B 6/4405; A61B 5/055; A61B 6/547; G16H 40/20; G16H 40/67
See application file for complete search history.

(56) References Cited

U.S. PATENT DOCUMENTS

| | | | | |
|---|---|---|---|---|
| 6,659,939 | B2 * | 12/2003 | Moll | A61B 34/35 600/102 |
| 2009/0010383 | A1 | 1/2009 | Fuhrmann | |
| 2012/0161675 | A1 | 6/2012 | Ding et al. | |
| 2014/0297130 | A1 | 10/2014 | Griffiths et al. | |
| 2017/0007342 | A1 * | 1/2017 | Kasai | A61B 34/30 |
| 2019/0125292 | A1 * | 5/2019 | Nebosis | A61B 6/4452 |
| 2020/0139544 | A1 | 5/2020 | Negishi et al. | |
| 2021/0369529 | A1 | 12/2021 | Mankin | |
| 2023/0311314 | A1 * | 10/2023 | Zeidler | A61B 50/24 700/254 |
| 2023/0337993 | A1 * | 10/2023 | Inglese | A61B 6/584 |

FOREIGN PATENT DOCUMENTS

| | | | |
|---|---|---|---|
| DE | 102007032533 | A1 | 1/2009 |
| DE | 102011057074 | A1 | 6/2012 |
| DE | 102013219744 | A1 | 10/2014 |
| DE | 102018126022 | B3 | 12/2019 |

* cited by examiner

S11
POS1
POS2
S12
BES
S13
S21
POSA;
VK
S23
S24
MOTK
S22
S30
SIG
S40
Δt 10
30
PS2
AE
G
M
PS1 BS
23
SE
21
22

BES
GES
POSA
VK
[s]

MOTION CONTROL FOR A MEDICAL INSTALLATION

CROSS-REFERENCE TO RELATED APPLICATION(S)

The present application claims priority under 35 U.S.C. § 119 to European Patent Application No. 22165569.9, filed Mar. 30, 2022, the entire contents of which are incorporated herein by reference.

FIELD

One or more example embodiments of the present invention relates to a motion control for a medical installation, specifically for a movable component of the medical installation. One or more example embodiments of the present invention determines a position spacing of two position sensors of the component and derives a manual operating force from said position spacing.

RELATED ART

In medical installations such as medical imaging installations, radiography, computed tomography, magnetic resonance tomography, ultrasound or the like, or installations for medical treatment such as irradiation or intervention for example, movable components are frequently provided which are moved during a medical workflow. For example, prior to an image data capture using X-ray technology the radiation source, the X-ray detector and the patient or the body region to be examined must be positioned relative to one another. To this end the patient couch on which the patient is placed for the examination, the radiation source and/or the detector can for example be moved individually. An adjusting motion can be performed purely manually, in other words via an operating force, with motorized assistance or fully automatically or autonomously. A manual adjusting motion is in this case particularly cost-effective, since drives and guidance devices can be dispensed with. In addition, a manual adjusting motion offers a particularly natural and intuitive operating feel for the user.

However, in the case of large and heavy components a manual adjusting force is no longer sufficient in order to move the component conveniently. A particularly large amount of force is then required to set the component in motion from a position of rest. This is the case for example if entire medical installations, for example a mobile C-arm installation, have to be moved. In particular this is also the case for a patient couch. Depending on the weight of the patient, a manually manageable total mass, which lies in the region of 100 kg to 200 kg, is easily exceeded.

Using high-quality and generally high-priced guidance systems, high operating forces can nowadays be reduced.

Alternatively, operating elements are integrated on the movable component and are fitted with force sensors. A sensor signal corresponding to a detected operating force is used to control an active, motorized drive. In this case on the one hand the natural operating feel is lost, since the main load for the motion of the component is provided by the motorized drive. In addition, the operating element, including the force sensor system, is fixed in place. An adjusting motion can only be initiated by touching this operating element.

SUMMARY

In contrast, one or more example embodiments of the present invention provide alternative means to permit userfriendly, cost-effective and flexible motion control for a medical installation or one of the components thereof.

One or more example embodiments of the present invention provide a method and a corresponding system for controlling a motion of a component of a medical installation along with a corresponding medical installation in accordance with the independent claims. Preferred and/or alternative, advantageous embodiment variants form the subject matter of the dependent claims.

Inventive achievements are described below with reference to the claimed method and also with reference to the claimed devices. Features, advantages or alternative forms of embodiment mentioned here can likewise also be applied to the other claimed subject matters and vice versa. In other words, objective claims (which are directed at a method, for example) can also be developed using features described or claimed in connection with one of the devices. The corresponding functional features of the method are in this case formed by corresponding physical modules or units.

According to one or more example embodiments, a method for controlling a motion of a component of a medical installation includes capturing a first position parameter via a first position sensor, the first position sensor being on the component; capturing a second position parameter via a second position sensor, the second position sensor being on the component; determining, by a control unit, a position spacing for the position sensors based on the first position parameter and the second position parameter; and generating a control signal for a drive unit of the component based on the determined position spacing.

According to one or more example embodiments, the method further includes assigning an adjusting force acting on the component to the determined position spacing, wherein the generating the control signal is based on the assigned adjusting force.

According to one or more example embodiments, the generating the control signal includes ascertaining a torque specification for the drive unit based on an absolute value of the assigned adjusting force for motorized power assistance.

According to one or more example embodiments, the capturing the first position and the capturing the second position occurs simultaneously.

According to one or more example embodiments, the method further includes capturing, via an acceleration sensor, an acceleration parameter of the drive unit simultaneously during the capturing the first position parameter and the capturing the second position parameter; determining a motorized input of force of the drive unit based on the acceleration parameter; and correcting the adjusting force based on the motorized input of force.

According to one or more example embodiments, the correcting corrects the adjusting force by subtracting of the motorized input of force.

According to one or more example embodiments, the generating the control signal includes generating, based on the position spacing, a torque specification for the drive unit for direction-dependent friction compensation.

According to one or more example embodiments, the method is carried out repeatedly with a time interval.

According to one or more example embodiments, the determining the position spacing includes subtracting a previously defined offset specific to the component and representing a non-elastic deformability of the component if a sign of the position spacing changes between two iterations of the method.

According to one or more example embodiments, a system for controlling a motion of a component of a medical installation includes a first position sensor on the component, the first position sensor configured to capture a first position parameter; a second position sensor on the component, the second position sensor configured to capture a second position parameter; and a control unit configured to, determine a position spacing for the first position sensor and the second position sensor based on the first position parameter and the second position parameter, and generate a control signal for a drive unit of the component based on the determined position spacing.

According to one or more example embodiments, the first position sensor and the second position sensor are on the component such that the first position sensor and the second position sensor have a maximum spacing at rest to one another along a spatial axis.

According to one or more example embodiments, the system includes pairs of the first position sensor and the second position sensor for each spatial axis, wherein the control unit is configured to generate a position spacing for the position sensor pairs of each spatial axis and a respective control signal for the drive unit of each spatial axis based on the respective position spacing.

According to one or more example embodiments, the first position sensor is a rotary encoder of the drive unit.

According to one or more example embodiments, a medical installation includes the component, the component being movable; the drive unit; and the system according to one or more example embodiments.

According to one or more example embodiments, the component is a stand to support an imaging unit or a patient table.

BRIEF DESCRIPTION OF THE DRAWINGS

Features and advantages of this invention and the manner in which they are achieved will become clearer and more readily understandable in connection with the following description of the exemplary embodiments, which are explained in greater detail in connection with the drawings. This description does not entail any restriction of the invention to these exemplary embodiments. The same components are provided with identical reference characters in different figures. The figures are generally not to scale. In the drawings.

DETAILED DESCRIPTION

Figure 1:
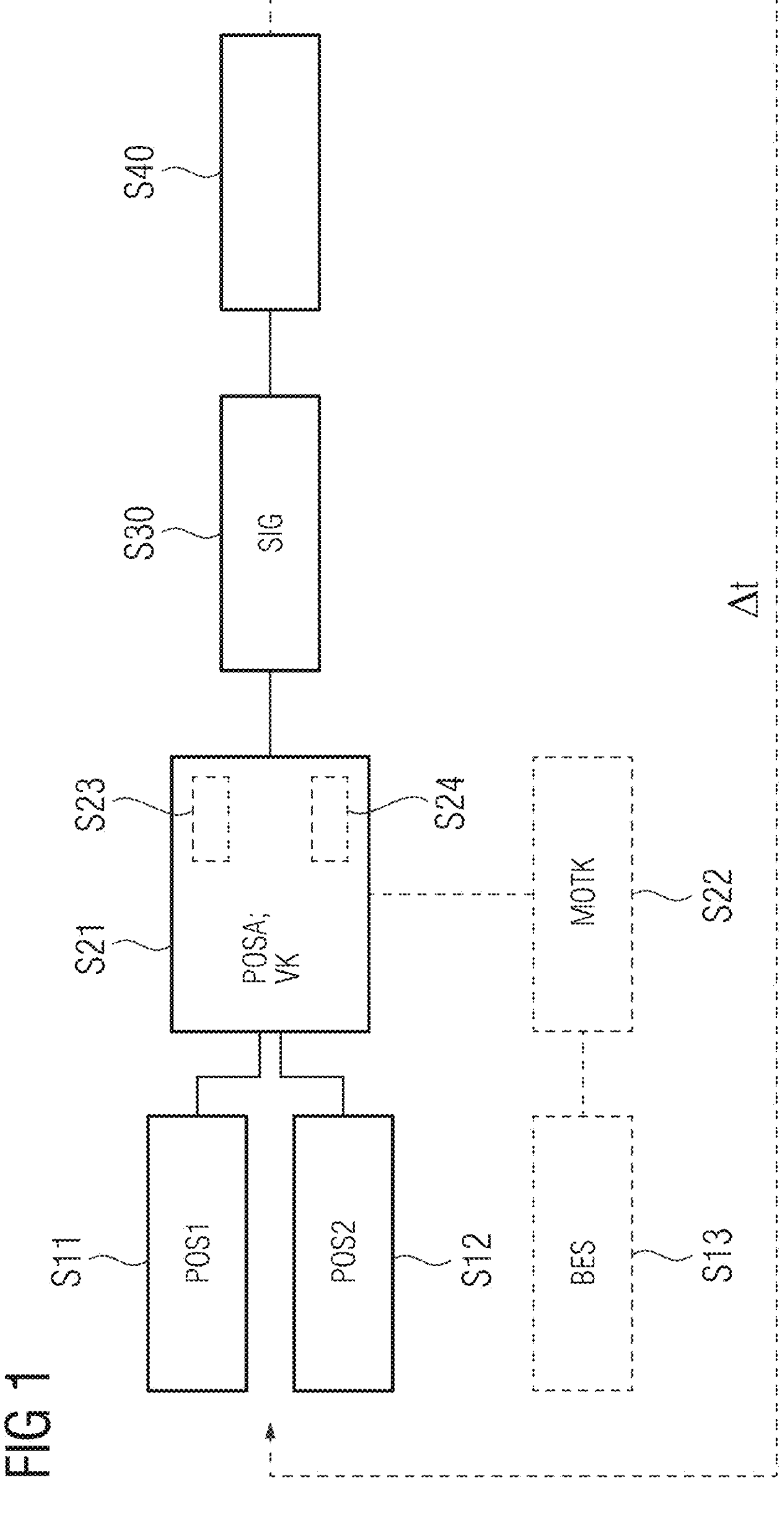
FIG. 1 shows a schematic flow diagram of an inventive method in one embodiment.

One or more example embodiments of the present invention relates to a method for controlling a motion of a component of a medical installation. The method comprises a plurality of steps. In a first step a first position parameter is captured via a first position sensor arranged on the component. In a second step a second position parameter is captured via a second position sensor arranged on the component. In a third step a position spacing for the position sensors is captured on the basis of the first and the second position parameter via a control unit. In a further step a control signal for a drive unit of the component is generated on the basis of the determined position spacing via the control unit.

Accordingly one or more example embodiments of the present invention is directed at a system for controlling a motion of a component of a medical installation. The system comprises a first position sensor arranged on the component, designed for the capture of a first position parameter, a second position sensor arranged on the component, designed for the capture of a second position parameter, and a control unit. This is designed for the capture of a position spacing for the position sensors on the basis of the first and the second position parameter, and for the generation of a control signal for a drive unit of the component on the basis of the determined position spacing.

One or more example embodiments of the present invention relates to a medical installation. This comprises at least one movable component. In some embodiments the medical installation itself as a whole forms the movable component. The medical installation further comprises a drive unit and an inventive system for controlling a motion of the component. In further embodiments of the invention the drive unit can also be designed as an integral part of the movable component.

The medical installation can be designed as a medical imaging installation, but also as an installation for medical treatment or intervention. For example, the medical installation is a radiography installation, in which digital X-ray images can increasingly be generated using X-ray radiation. However, a computed tomography installation, a magnetic resonance tomography installation or the like may also be involved. The medical installation comprises a movable component, preferably multiple movable components. A movable component in this case means a unit of the installation that can be moved relative to other units of the installation or to the area surrounding the installation. The movable component can be moved manually, with motorized assistance via the drive unit or on a fully motorized basis. In preferred embodiments of the invention the motion relates to a translational motion along a spatial axis. A movable component can however also be translationally adjustable along multiple spatial axes, so that the overall motion of the component ensues as an overlap of the individual translational motions.

The inventive system for controlling a motion is advantageously integrated into the medical installation. Alternatively, at least individual units of the system, in particular the control unit or submodules thereof, can be arranged remotely or in isolation. The inventive system can be designed in particular to perform the step of determining a position spacing and the step of generating a control signal, but also the entire inventive method, for a medical installation.

In some embodiments of the invention a movable component can be designed as a stand, for example a Bucky wall stand or a ceiling-mounted stand, or as a patient couch or the stretcher board arranged thereon. Bucky wall stands and ceiling-mounted stands are typically used to fasten and position imaging units such as an X-ray source and/or an X-ray detector. The patient couch is used for receiving or supporting and positioning a patient.

In a preferred embodiment an inventive drive unit is designed as a linear drive. This preferably comprises an electric motor or a rotary servomotor which drives a shaft in a rotary manner and the rotation of which is translated into a linear motion of the component via a corresponding gearing mechanism. Alternative drive concepts are likewise conceivable and are within the scope of the invention. In some embodiments the drive unit also comprises an auxiliary drive which is designed to effect direction-dependent friction compensation.

In an adjusting motion the drive unit can also be moved as an integral part of the component or at least partially designed to be stationary relative to a further unit of the medical installation.

Two position sensors different from and independent of one another are provided in accordance with one or more example embodiments of the present invention. Each position sensor is designed to capture position information corresponding to its spatial position and on the basis of the position information to generate a position parameter which can be further processed and which is transferred to a control unit of the inventive system. In this respect the capture of a position parameter also describes a capture by or transmission of the position parameter from a position sensor to the control unit.

In a preferred embodiment the position parameters are to be understood as position specifications that are specified in respect of the same coordinate system, for example the installation coordinate system. This typically involves a three-dimensional coordinate system.

In a particularly preferred embodiment the position parameters are one-dimensional.

One or more example embodiments of the present invention assumes that both the position sensors are remote from one another, in particular remote from one another along a spatial axis on which components are arranged or integrated and the captured position parameters always differ.

Next the control unit determines a position spacing, in particular a position spacing along a spatial axis. It is thus determined how far both position sensors are spaced apart from one another. The determined position spacing in this case comprises an absolute spacing, but by way of its sign also comprises information relating to the location of the position sensors relative to one another and thus also comprises a specification of direction for the manual operating force.

One or more example embodiments of the present invention further assumes that the determined position spacing is a variable dependent on a manual operating force introduced into the movable component and acting along the spatial axis. In other words, one or more example embodiments of the present invention assumes that the determined position spacing changes in the direction of the spatial axis with the operating force of a user. This procedure is based on the assumption that the movable component is designed as an elastic, i.e. reversibly deformable, element, wherein the elastic deformation of the component is caused by, or is substantially caused by, the operating force introduced manually by the user.

Using the thus determined position spacing one or more example embodiments of the present invention enables a conclusion to be drawn about the manual operating force acting on the component. Correspondingly, in a further step a control signal for the drive unit is generated on the basis of the determined position spacing. In preferred embodiments of the invention the generation of the control signal comprises assigning an adjusting force corresponding to the manual operating force to the position spacing. In other embodiments the position spacing is used directly to generate a control signal corresponding to the associated adjusting force. The intermediate step is omitted in these embodiments.

In a preferred embodiment the adjusting forces assigned to the position spacings are specific to the movable component. Thus one or more example embodiments of the present invention advantageously takes account of the fact that each component can have a different elastic deformation behavior. The elastic deformation behavior is in this case for example dependent on the basic shape, the choice of materials and/or the size of the movable component. A compact, heavy component will for example have a greater rigidity than an elongated, thin or light component.

The present invention advantageously replaces a force sensor, in order to capture a manual operating force in terms of its direction and/or absolute value. The cost of the force sensor is therefore eliminated. Furthermore, one or more example embodiments of the present invention enables a manual operating force to be applied at any point on the movable component. This corresponds to a procedure as is also used for a purely manual adjusting motion. Since there is no need to implement a force sensor, the user can now apply the manual operating force at any point on the component and is not restricted to the operating element comprising the force sensor.

In some embodiments the first and the second position sensor are arranged on the component such that they have a maximum spacing at rest from one another along a spatial axis.

The spacing at rest describes the spacing of both sensors when the component is not moving and when no force is acting on the component.

The further both the position sensors are spaced apart from one another, the more accurately can the elastic deformation behavior of the component be represented via the position spacing. However, in further embodiments an arrangement of the position sensors inside the drive train is more appropriate. For example, the first position sensor is installed directly in or on the drive, in other words the drive unit, wherein the second position sensor is arranged in or on the output side, advantageously on a rear part of the output side. For example, the second position sensor is then arranged on the drive shaft of the drive unit, in other words in particular behind a gearing mechanism of the drive unit.

Particularly advantageous are embodiments of the invention in which for the capture of the position parameters use is made of position sensors which are in any case installed in the medical installation or the movable component, for example the position sensors which are employed to ensure first-fault-protected operation of the medical installation. In this way additional components can be omitted and extra costs saved.

Particularly advantageous embodiments of the invention correspondingly provide that the first position sensor is for example designed as a rotary encoder of the drive unit. The rotary encoder is a fixed part of the drive unit, which for the correct exercise of the motor function continuously captures the angular position of the motor. By using the angular position and monitoring the revolutions of the motor, position information can be provided in the form of a position parameter.

The second position sensor or in alternative embodiments of the invention both position sensors can be designed in any other manner known per se. For example, a position sensor can be designed as a laser sensor, an inductive sensor, an ultrasound sensor, a capacitive sensor or the like.

The control unit is designed to determine a position spacing on the basis of the position parameters and to generate a control signal for the motion control of the component on the basis of the position spacing. The position spacing is representative of a manual operating force applied to the component. Hence the control signal is suitable for controlling the component in accordance with the manual operating force. The control unit comprises an interface for the input or capture of the position parameters and for the output of the control signal to the drive unit. The interface can preferably be designed as an integral input and output interface.

In some embodiments of the invention the control unit can be designed as one or more central and/or local computing modules. The computing modules can each have one or more processors. A processor can be designed as a central processing unit (CPU/GPU). The control unit can in particular comprise a motor controller of the drive unit. In further embodiments the motor controller is designed as part of the drive unit. The control unit further comprises an evaluation module or an evaluation unit, which processes the position parameters and generates a control signal on the basis of the determined position spacing.

In preferred implementations the control unit is in turn implemented as a part or module of a central computing unit of the medical installation. In some implementations the control unit can be designed as a submodule of the central computing unit or vice versa. Alternatively, the control unit can be implemented as a local or cloud-based processing server. The control unit can further comprise one or more virtual machines.

The interface of the control unit can generally be designed for the exchange of data between position sensors and drive unit and the control unit and/or for the exchange of data by modules of the control unit with one another. The interface can in this respect be implemented in the form of one or more individual data interfaces, which can have a hardware and/or software interface, a data bus, for example a PCI bus, a USB interface, a FireWire interface, a ZigBee or a Bluetooth interface.

In particular the evaluation module and the motor controller are connected to one another via a data bus. The interface can further have an interface of a communication network, wherein the communication network can have a Local Area Network (LAN), for example an Intranet or a Wide Area Network (WAN). Accordingly the one or more data interfaces can have a LAN interface or a wireless LAN interface (WLAN or Wi-Fi).

The control unit of the system is particularly preferably designed to carry out an evaluation of position parameters for different spatial axes. In this case two position parameters are captured in each case for the various spatial axes, position spacings are determined and control signals for motion control along the multiple spatial axes are generated. In some embodiments of the inventive system a pair can accordingly consist of a first and second position sensor for each spatial axis. At the same time the control unit is then designed to generate a position spacing for the position sensor pairs of each spatial axis and a respective control signal for the drive unit of each spatial axis on the basis of the respective position spacing.

In some embodiments the system accordingly comprises at least one drive unit per spatial axis.

It is particularly advantageous, since it saves on components, if multidimensional position sensors are used which can supply position parameters relating to multiple spatial axes. In the arrangement with multidimensional position sensors a compromise must advantageously be found, so that for all captured spatial axes the elastic deformation behavior can be represented using the position spacings.

In an advantageous embodiment the method comprises an assignment of an adjusting force acting on the component to the determined position spacing, wherein the generation of the control signal for the drive unit takes place on the basis of the assigned adjusting force.

To this end an exchange of data between the control unit and an internal or external memory unit can be included, in which different position spacings from the movable component are assigned adjusting forces that are retrievable in particular for the evaluation module or the evaluation unit, for example in the form of a look-up table. Alternatively or additionally it can be provided that the evaluation module carries out an interpolation or extrapolation step on the basis of available data pairs, in order to derive an associated adjusting force.

The memory unit can now comprise a further look-up table which creates a correlation between the adjusting force and corresponding control information, on the basis of which the control signal is derived. The control information is for example present as a torque specification, speed specification or position specification for the drive unit, corresponding to the adjusting force.

In other embodiments the memory unit can, for example via a look-up table, create a direct correlation between the determined position spacing and corresponding control information.

Particularly advantageously, the generation of the control signal for the drive unit comprises determining a torque specification for the drive unit on the basis of the absolute value of the assigned adjusting force for motorized power assistance. A torque specification offers the advantage for the user, compared to other control information, of an authentic operating feel. In other words the value of the torque specification complies with the absolute value of the position spacing. In further embodiments the control information can however also be present in the form of a position specification and/or a speed specification for the drive unit. This can for example again be specified by the type of component or the type of drive unit.

The determined position spacing preferably also comprises direction information in respect of the manual operating force. In this respect one or more example embodiments of the present invention enables not just a torque specification, but also a specification of the direction of motion for the drive unit in accordance with the direction of the manual operating force via a control signal. Besides the torque specification, the direction of rotation for the drive unit can preferably also be generated as control information.

To be able reliably to draw conclusions about the manual operating force on the basis of the position spacing, the position sensors must simultaneously capture their position parameters and transmit them to the control unit. Accordingly, in some embodiments of the invention it is provided that the capture of the first and the second position parameter takes place simultaneously. In the context of the invention, simultaneously should be understood as "with the smallest possible time offset".

For this purpose, both position sensors are preferably connected to and read out via the motor controller. The motor controller is inventively configured such that it transmits the first and second position parameter in one and the same data packet, also called a telegram, to the evaluation module of the control unit via the data bus for further processing. This prevents a time offset from arising due to multiple data packets being sent consecutively via the data bus.

In certain situations it may be that a manual operating force is applied to the component while it is already moving, for example in order to initiate a change of direction or an acceleration of motion, wherein the current motion can be ascribed to a motorized input of force. Accordingly, in a preferred implementation the inventive method comprises a capture of an acceleration parameter of the drive unit simultaneously with the capture of the first and the second position parameter. Furthermore, the motorized input of force of the drive unit is determined on the basis of the acceleration parameter, and thus the adjusting force is corrected.

In a preferred embodiment in this case the correction of the adjusting force is effected by subtraction of the determined motorized input of force.

This procedure is based on the assumption that the proportion of force in the adjusting force, in other words the corrected adjusting force, that is not introduced by the drive unit can be ascribed solely to the operating force exerted manually by the user.

To calculate the motorized input of force the acceleration parameter, a variable on the basis of which a value for a current acceleration of the drive unit can be determined, is used to determine the effective acceleration and is multiplied by the moving mass of the component. The component mass can in this case be provided to the control unit or the evaluation module as a fixed mass parameter, for example by the memory unit described in the introduction.

The procedure described enables the adjusting force to be better adjusted to the actual manual operating force. In this embodiment the control signal is generated on the basis of the corrected adjusting force.

In some embodiments the inventive system therefore also comprises an acceleration sensor, which is preferably integrated into the drive unit or interacts with it. The acceleration sensor can for example be designed as a MEMS sensor known per se, as a strain gauge or as a piezo-electric acceleration sensor.

The acceleration parameter is advantageously captured simultaneously with the first and second position sensor and is transmitted with the same data packet to the evaluation module of the control unit via the motor controller in order to ensure simultaneity.

Alternative embodiments in which the position spacing is converted directly into a control signal corresponding to the associated adjusting force can, on the basis of the motorized input of force determined as described above, also derive a motorization-related position difference, and thus perform a correction of the position spacing (likewise by subtraction). The control signal for the drive unit is then generated on the basis of the corrected position spacing.

As mentioned in the introduction, the position parameters comprise information relating to the effective direction of the manual operating force, so that on the basis of the determined position spacing the manual operating force can be determined not just in terms of the absolute value, but also in terms of its direction (forward or backward along the spatial axis). The effective direction is in this case substantially defined by the sign of the determined position spacing. In situations in which the adjusting force cannot reliably be determined in accordance with the absolute value, the generation of the control signal for the drive unit can at least comprise, on the basis of the sign of the position spacing, a torque specification for the drive unit, in particular the auxiliary drive, for direction-dependent friction compensation. The drive unit is here consequently controlled such that it exerts a motorized drive force on the component in the corresponding direction, which is sufficient to overcome the mass-related static friction. Also to this end, the evaluation module or the evaluation unit can again access the retrievably stored mass parameters of the component. Alternatively, the required torque specific to the component mass can also be stored directly in the memory unit.

In alternative embodiments a direction-dependent position specification or speed specification for the drive unit can also be generated as a function of the embodiment of the drive unit.

In order to monitor the medical installation continuously and to check on a manual input of force, in particularly preferred implementations the inventive method is repeated and particularly preferably is carried out with a time interval of for example 5 ms or 10 ms. Other time intervals are likewise possible and are within the scope of the invention. The time interval selected can in particular again depend on the movable component and for example the typical motion behavior thereof. In other words, position parameters and if appropriate acceleration parameters are regularly retrieved by the corresponding sensors and are evaluated by the control unit. In this way changes to the manual operating force (in respect of absolute value and/or direction) are substantially recorded without a time delay and adjustments are performed in respect of the motorized motion control or motion regulation.

Further embodiments of the inventive method provide that the determination of the position spacing comprises subtracting a previously defined offset, specific to the movable component of the medical installation, representing a non-elastic deformability of the component, if the sign of the position spacing changes between two passes of the method.

This procedure is based on the finding that the movable component is deformed by a (manual) input of force not just elastically, but also non-elastically. This non-elastic deformation can for example be based on component tolerances, a bearing clearance between two interlocking parts of the component or the like, in particular on tolerances of the drive unit, so that when force is exerted parts of the component can be moved relative to one another. This non-elastic deformation, for example in the form of a change in length of the component or a change in position of one of the position sensors in the spatial axis in question, occurs whenever the direction of motion of the component is changed, in other words when the sign of the position spacing changes. It cannot be ascribed to the manual operating force itself. The non-elastic deformation is in turn specific to the structure or the individual integral parts of the movable components and can be determined experimentally beforehand and saved as a fixed length parameter for the evaluation module.

In this embodiment the method hence advantageously comprises a step of comparing a sign of the position spacing between two passes of the method. Furthermore, the method in this embodiment also comprises monitoring the direction of motion of the drive unit. Comparing the sign and monitoring the direction of motion are preferably carried out for each pass of the method, in other words continuously. If the sign changes, then during the determination of the position spacing preferably half of the length parameter, taking into consideration the direction of motion, is added to or subtracted from one of the position parameters or the position spacing, preferably across the board. Also as a result of this the manual operating force actually introduced is mapped more accurately using the determined position spacing.

One or more example embodiments of the present invention further relates to a computer program containing program code, in order to carry out the inventive method for controlling a motion of a component of a medical installation if the computer program is executed on a computer.

One or more example embodiments of the present invention further relates to a computer-readable data medium containing program code of a computer program, in order to carry out the inventive method for controlling a motion of a component of a medical installation if the computer program is executed on a computer. In particular the determination of the position spacing or the generation of the control signal on the basis of the position spacing can advantageously be executed on a computer, for example a computing unit of the medical installation.

FIG. 1 shows a schematic flow diagram of an inventive method in one embodiment. The method is used to control a motion, in particular an adjusting motion of a component 30 of a medical installation 10.

In a first step a capture S11 of a first position parameter POS1 via a first position sensor PS1 arranged on the component 30 takes place.

In a second step a capture S12 of a second position parameter POS2 via a second position sensor PS2 arranged on the component takes place.

Both position parameters POS1 and POS 2 are designed such that on the basis of their values a location and/or position in relation to a reference coordinate system, preferably the coordinate system of the medical installation 10, can be inferred. In the simplest case the position parameters POS1 and POS2 directly indicate the position of the associated position sensor PS1, PS2.

A further step S21 is directed at a determination of a position spacing POSA for the position sensors PS1, PS2 on the basis of the first and the second position parameter POS1, POS2 via a control unit SE. Both position sensors PS1, PS2 are characterized in that they are arranged on the movable component 30, but in different positions in each case (at least in respect of a spatial axis). One or more example embodiments of the present invention assumes that the position spacing POSA between both the position sensors PS1 and PS2 is a variable dependent on a manual operating force acting on the component. In other words, one or more example embodiments of the present invention assumes that the movable component is elastically deformable and the change in the position spacing POSA is based on said elastic deformability.

On the basis of the determined position spacing POSA one or more example embodiments of the present invention in the further course of the method establishes a correlation between the determined position spacing POSA and the manual operating force being exerted.

Accordingly, in a further method step S30 a control signal SIG for a drive unit AE of the component 30 is generated on the basis of the determined position spacing POSA. This means that a control signal for the motion control of the component 30 is generated, which corresponds to the exertion of manual force determined via the determined position spacing.

Step S21 can in some embodiments also comprise, besides the determination of the position spacing POSA, an assignment of an adjusting force VK acting on the component to the determined position spacing POSA. This is then followed by the generation of the control signal SIG for the drive unit AE on the basis of the assigned adjusting force VK. In this case a value for the adjusting force VK is explicitly determined by the control unit SE and in the further course of the method this is taken as the basis for the generation of the control signal SIG. For this purpose the control unit SE for example accesses an internal memory, where values for the adjusting force VK that are specific to the movable component 30 are stored for different position spacing values. Alternatively, via a retrievable calculation rule corresponding to a likewise component-specific, functional correlation between position spacing POSA and adjusting force VK, the control unit SE can also itself calculate a value for the adjusting force VK.

Both variants for the generation of the control signal SIG on the basis of the position spacing POSA or the adjusting force VK are equivalent. The control signal SIG is in this case designed as a control signal for the drive unit AE. It is designed to effect or trigger motorized motion assistance and/or friction compensation.

Accordingly the control signal SIG for the drive unit SE is preferably generated in step S30, in that a torque specification for the drive unit AE is ascertained for the motorized power assistance on the basis of the absolute value of the assigned adjusting force VK and/or of the determined position spacing POSA. Friction compensation can, in contrast, already be performed on direction information, in other words the sign, of the position spacing POSA or the adjusting force VK via an auxiliary drive of the drive unit AE. This is in particular advantageous for situations in which the adjusting force VK cannot be determined accurately. In such situations the drive unit AE can nevertheless be used to To determine the position spacing POSA or the adjusting force VK as exactly as possible, steps S11 and S12 for the capture of the first and the second position parameter POS1, POS2 are preferably executed simultaneously. The smaller the time offset between the capture of both the position parameters POS1, POS2, the more accurately the determined position spacing POSA represents the manual operating force currently being exerted. The simultaneity is ensured in some embodiments of the invention, in that the position parameters POS1, POS2 are retrieved or transmitted for example via the motor controller 23 of the drive unit AE or are sent within the same data packet.

In an optional step S13 of the inventive method an acceleration parameter BES of the drive unit AE is also captured in addition to the position parameters POS1, POS2. The acceleration parameter BES provides information on whether and with what acceleration the movable component 30 is moving. The acceleration parameter BES consequently indicates the motion status of the movable component 30. The acceleration parameter BES is preferably captured via an acceleration sensor BS arranged on the drive unit AE of the component 30. The acceleration parameter BES consequently indicates a proportion of motion of the component 30 that can be ascribed to the drive unit AE. Step S13 too advantageously takes place simultaneously to the capture of the first and the second position sensor POS1, POS2.

Further, in a further optional step S22 a motorized input of force MOTK of the drive unit AE is determined on the basis of the acceleration parameter BES. To this end, the motor force is ascertained on the basis of the moving mass of the component 30, which is known to the inventive system, for example is retrievably stored in the memory, and on the basis of the effective acceleration. In order to ascertain the currently effective manual operating force accurately, the motorized input of force MOTK is used in a likewise optional step S23 to correct the adjusting force VK. The correction takes place in that the motorized input of force MOTK is deducted from the adjusting force VK. During the subtraction, account is taken of absolute values and signs of the calculated forces.

A further optional step S24 provides for a previously defined offset O specific to the movable component 30 of the medical installation 10 and representing a non-elastic deformability of the component 30 to be subtracted if the sign of the position spacing POSA changes between two passes of the method. Using this optional step the determination of the manual operating force currently being exerted is improved still further, since thanks to the offset one or more example embodiments of the present invention further takes into consideration non-elastic deformation proportions of the component 30, which can likewise be caused by the manual operating force. The offset is for example again retrievably present in a memory unit as an offset value that was previously established and that can be ascertained experimentally and is specific to each component. The non-elastic deformation occurs or can be observed whenever the movable component changes its direction of motion. If the motion continues in the same direction the deformation is retained. In this respect the offset O is taken into consideration in the determination of the adjusting force VK whenever a change of sign has been established for the position spacing POSA in a loopback within step S21. If there is no change of sign between two method loops, step S24 is not carried out. In a preferred embodiment the offset can be designed as a value representing a change in length of the component 30 in the spatial axis in question.

In a further step S40 the generated control signal SIG is transmitted to the drive unit AE, in particular for example thereto via a motor controller 23 of the drive unit AE, to be executed.

For the purposes of continuous motion control the inventive method is repeatedly carried out with a time interval Δt. This means that the positions of the position sensors PS1, PS2, the motorized acceleration and/or the like exercised by the drive unit AE are monitored over a period, for example over the entire duration of operation of the medical installation, and are evaluated for the motion control. In a preferred embodiment the capture of the position parameters takes place with a time interval of between 3 ms and 15 ms, particularly preferably the capture of the position parameters POS1, POS2 takes place with a time interval of between 5 ms and 10 ms. Using these time intervals, it was possible in trials to create a particularly intuitive and direct operating feel for the user.

Figure 3:
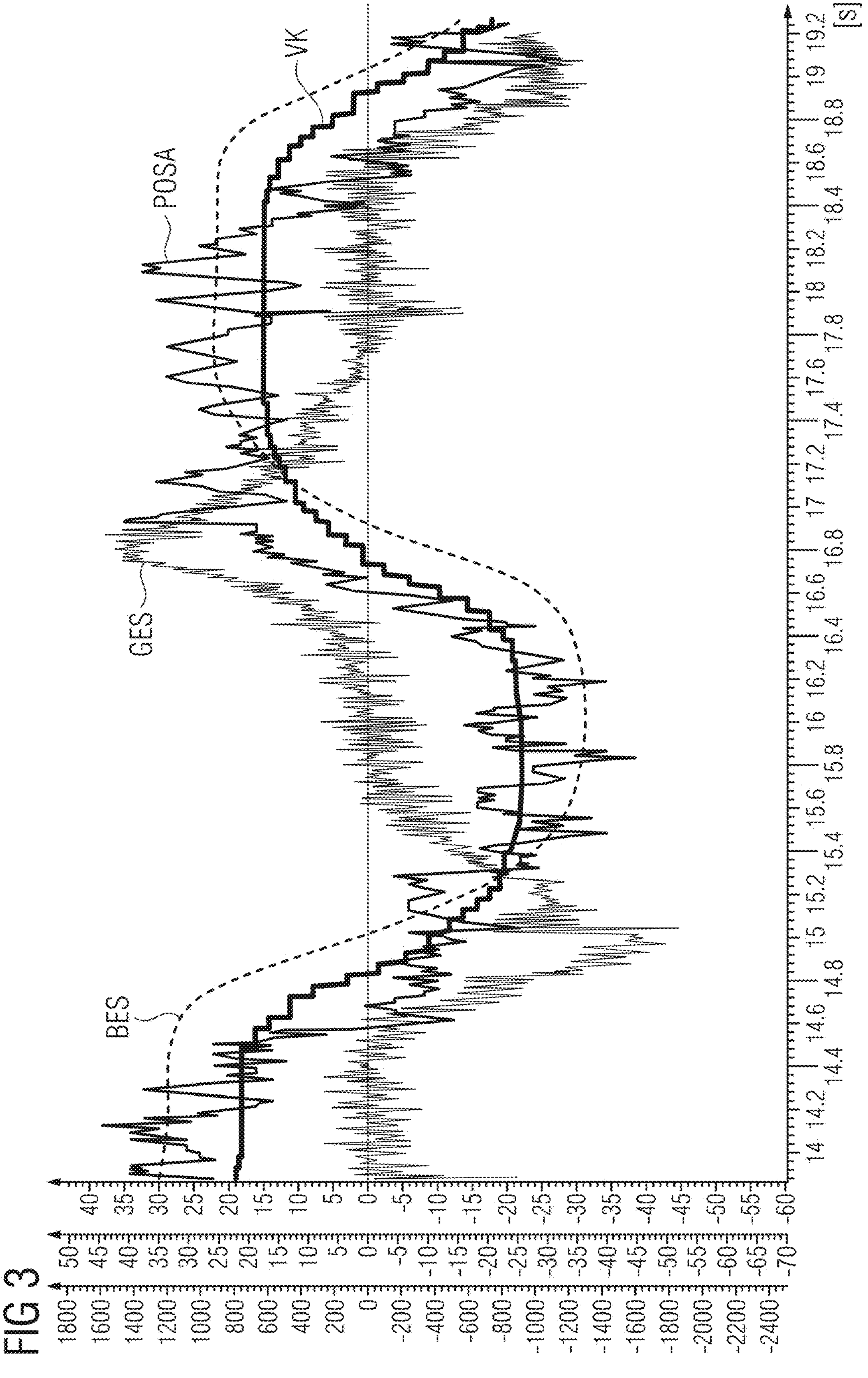
FIG. 3 shows a diagram representing a time curve of the position spacing in connection with the determined adjusting force, a motorized acceleration and a speed of motion of the component in one embodiment of the invention.

FIG. 3 shows in this connection a diagram representing a time curve of the position spacing POSA in relation to the adjusting force VK continuously determined therefrom. The period under consideration extends across approximately 5 s. In this case a motorized acceleration or the motorized input of force MOTK resulting therefrom as well as a component-specific offset have been taken into consideration in the event of a change in the direction of motion. Likewise also plotted in the diagram is the speed of motion of the component 30. It is apparent that the adjusting force VK follows the course of the (average) position spacing POSA with a slight offset.

Figure 2:
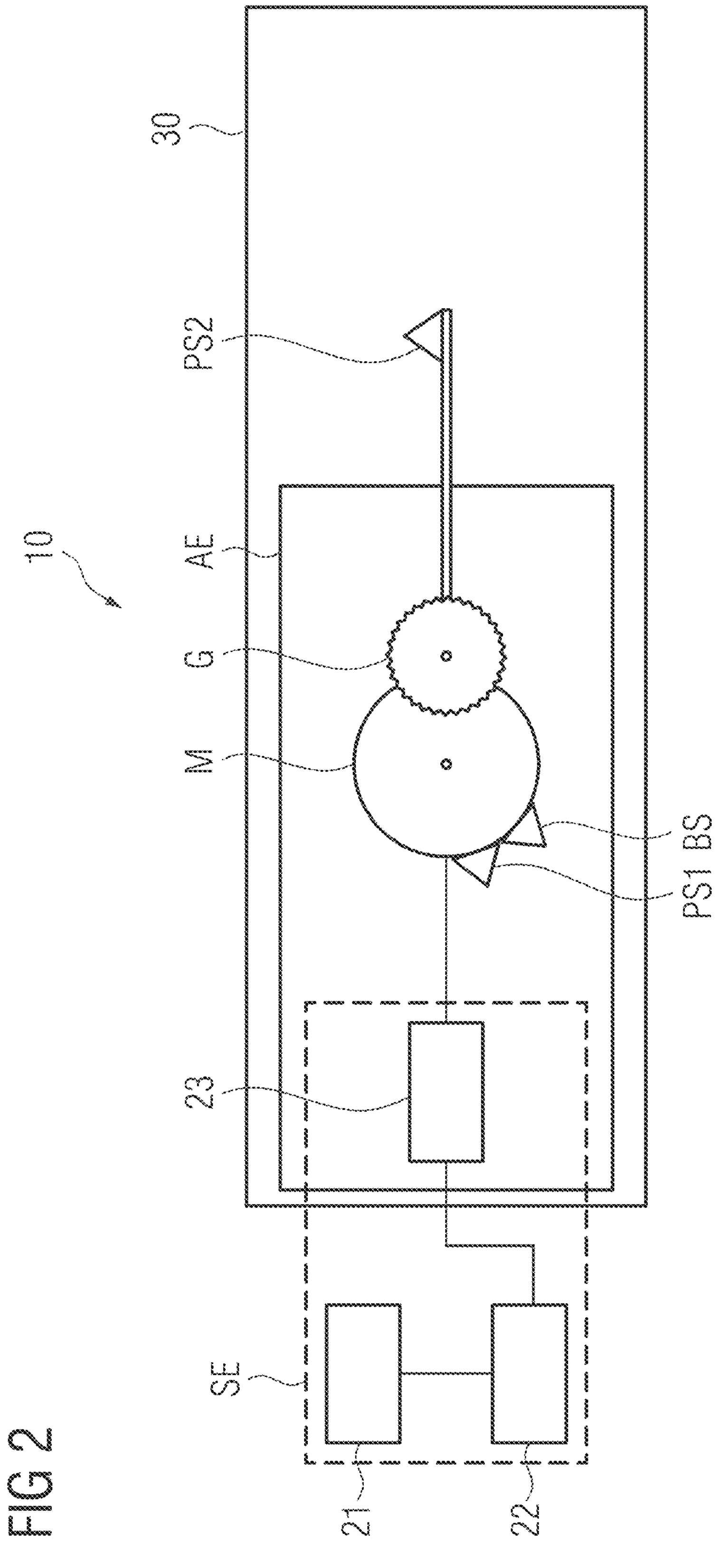
FIG. 2 shows a detailed view of a medical installation comprising an inventive system for control in one embodiment.

FIG. 2 shows a detailed view of a medical installation 10 comprising an inventive system for control in one embodiment. The medical installation comprises a movable or moving component 30. In a preferred embodiment the medical installation 10 is designed as a medical imaging installation, i.e. it is used to generate medical image data for a patient. Particularly preferably the medical installation 10 is a medical X-ray imaging installation which comprises an X-ray source and an X-ray detector (not shown). Specifically the medical installation is a radiography installation, with which conventional X-ray transmission acquisitions are generated. In these embodiments the movable component 30 of the medical installation 10 is preferably designed as a floor-mounted or ceiling-mounted stand to support an imaging unit such as the X-ray source or the X-ray detector.

The medical installation can however also be designed differently, for example as an installation for treatment or intervention. In other embodiments of the medical installation 10 the movable component 30 can preferably be designed as a patient couch, which is designed for supporting or positioning the patient.

The medical installation further comprises a drive unit AE and an inventive system for controlling a motion of the component 30.

The drive unit AE is in the present case designed as part of the component 30. In some embodiments of the invention the drive unit AE moves at least partially along with the components when they move. The drive unit AE as a drive element here comprises an electric motor M designed as a servomotor which in operation causes a rotational motion of its drive shaft in a translational motion of the component via a gearing mechanism G comprising at least one toothed wheel engaging into a toothed rack. In some embodiments the drive unit AE can further comprise an auxiliary drive (not shown), which is used for direction-dependent friction compensation.

The system for controlling a motion of the component 30 is designed to carry out steps S11 to S40 of the inventive method, in particular including the optional steps, as described above with reference to FIG. 1. The system for controlling a motion of the component 30 comprises a first position sensor PS1 arranged on the component 30. This is designed to capture a first position parameter POS 1. It further comprises a second position sensor PS2 arranged on the component, which is designed to capture a second position parameter POS2.

The first position sensor PS1 is here designed as a position encoder or rotary encoder PS1 of the electric motor M and in this respect is incorporated as standard in medical installations. The second position sensor PS2 is in the present case designed as a position sensor which is mounted on the output-side end of the toothed rack.

In principle the accuracy of the determination of the position spacing POSA or of the adjusting force VK can be increased if both the position sensors have the greatest possible, i.e. maximum, spacing to one another at rest, in other words are attached to the component 30 as far apart from one another as possible along the spatial axis in question. In this way the elastic deformation behavior of the component 30 can be optimally mapped using the position spacing.

The system further comprises an acceleration sensor BS, which is likewise installed directly on the motor M of the drive unit AE and captures an acceleration parameter BES of the motor M.

The system for motion control further comprises a control unit SE. This is designed to determine the position spacing POSA for the position sensors PS1, PS2 on the basis of the first and the second position parameter, POS1, POS2 and to generate a control signal SIG for the drive unit AE, in particular the motor M, on the basis of the determined position spacing POSA.

For this purpose the control unit SE can comprise an evaluation unit 21. This is designed to carry out all calculation, ascertainment and determination steps of the inventive method in connection with S21, S22, S23, S24 and S30.

The control unit SE further comprises a data interface for bidirectional communication between different units of the medical installation 10 and the control unit SE.

The evaluation unit 21 is designed to perform, via the interface 22, an exchange of data for the receipt of position and acceleration parameters POS1, POS2, BES as well as for the output of control signals SIG. In particular the interface 22 can set up a data connection between the evaluation unit and the motor controller 23 of the drive unit AE. The motor controller 23 inventively serves as a central communication or monitoring unit for the drive unit and for example ensures a substantially simultaneous transmission of the position parameters POS1, POS2 for each pass of the method.

Furthermore, the motor controller 23 can also be used to transmit the acceleration parameter BES to the evaluation unit 21 simultaneously.

Not shown here, but in the scope of the invention, the component 30 of the medical installation 10 can be designed to be moved along not just one but along multiple spatial axes. In this connection the system for motion control for each spatial axis can comprise a pair consisting of a first and second position sensor, wherein the control unit SE is then designed to generate a position spacing for the position sensor pairs of each spatial axis and a respective control signal for the drive unit of each spatial axis on the basis of the respective position spacing. In other words the control unit is designed to carry out the inventive method in respect of multiple spatial axes, in particular also simultaneously or overlapping in time. The interface 22 is accordingly designed to provide an exchange of data between the evaluation unit 21 and a motor controller 23 of the drive units AE provided for the multiple spatial axes/directions of motion.

The advantages of one or more example embodiments of the present invention are briefly summarized below:

One or more example embodiments of the present invention enables the capture of a manual operating force in terms of absolute value and direction, without a force sensor having to be provided for this in the medical installation. The cost of the force sensor can be saved. Furthermore, the present invention enables the manual operating force to be introduced into the movable component at any point, as a result of which the flexibility and intuitiveness during operation of the medical installation are increased. The operation is now no longer restricted to the region of the component in which the force sensor is installed, for example an operating handle or lever.

In some embodiments of the invention the first position parameter is captured via a sensor system which is installed in the drive unit as standard, for example the position encoder or rotary encoder of an electric motor. Since a medical installation typically has to be embodied as first-fault-protected and accordingly comprises, in addition to the actual control path, a protection path for the automatic control and monitoring of the control path, the second position parameter can also be captured using a redundant protection path sensor system installed as standard. Additional costs for the implementation of the inventive system for motion control can thereby advantageously be minimized.

Implementing a small auxiliary drive, which is used only for friction compensation for the support of a then substantially manual adjusting motion of the component, saves costs compared to servodrives, which take over the adjusting motion completely. If the evaluation unit outputs a control signal comprising a rotary torque specification for the motor of the drive unit, the system for motion control is therefore operated in rotary torque mode, and furthermore a synthetic operating feel for the user can be avoided, as would arise for example in the case of position or speed regulation.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term “and/or,” includes any and all combinations of one or more of the associated listed items. The phrase “at least one of” has the same meaning as “and/or”.

Spatially relative terms, such as “beneath,” “below,” “lower,” “under,” “above,” “upper,” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as “below,” “beneath,” or “under,” other elements or features would then be oriented “above” the other elements or features. Thus, the example terms “below” and “under” may encompass both an orientation of above and below. The device may be otherwise oriented (rotated 90 degrees or at other orientations) and the spatially relative descriptors used herein interpreted accordingly. In addition, when an element is referred to as being “between” two elements, the element may be the only element between the two elements, or one or more other intervening elements may be present.

Spatial and functional relationships between elements (for example, between modules) are described using various terms, including “on,” “connected,” “engaged,” “interfaced,” and “coupled.” Unless explicitly described as being “direct,” when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being “directly” on, connected, engaged, interfaced, or coupled to another element, there are no intervening elements present. Other words used to describe the relationship between elements should be interpreted in a like fashion (e.g., “between,” versus “directly between,” “adjacent,” versus “directly adjacent,” etc.).

The terminology used herein is for the purpose of describing particular embodiments only and is not intended to be limiting of example embodiments. As used herein, the terms “and/or” and “at least one of” include any and all combinations of one or more of the associated listed items. It will be further understood that the terms “comprises,” “comprising,” “includes,” and/or “including,” when used herein, specify the presence of stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items. Expressions such as “at least one of,” when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where not yet explicitly done, but where it makes sense and in connection with the invention, individual exemplary embodiments can combine or exchange their individual subsidiary aspects or features with one another without departing from the scope of the present invention. Advantages of the invention described in respect of one exemplary embodiment also, where transferrable, apply to other exemplary embodiments without being explicitly mentioned.

The invention claimed is:

1. A method for controlling a motion of a component of a medical installation, the method comprising:
- capturing a first position parameter via a first position sensor, the first position sensor being on the component;
- capturing a second position parameter via a second position sensor, the second position sensor being on the component;
- determining, by a control unit, a position spacing for the position sensors based on the first position parameter and the second position parameter; and
- generating a control signal for a drive unit of the component based on the determined position spacing, wherein the component is movable and elastic, and an elastic deformation of the component is caused by an operating force introduced manually by a user,
  - wherein the method is carried out repeatedly with a time interval, and
  - wherein the determining the positioning includes, subtracting a previously defined offset specific to the component and representing a non-elastic deformability of the component if a sign of the position spacing changes between two iterations of the method.

2. The method of claim 1, further comprising:
- assigning an adjusting force acting on the component to the determined position spacing, wherein the generating the control signal is based on the assigned adjusting force.

3. The method of claim 2, wherein the generating the control signal includes,
- ascertaining a torque specification for the drive unit based on an absolute value of the assigned adjusting force for motorized power assistance.

4. The method of claim 3, wherein the capturing the first position and the capturing the second position occurs simultaneously.

5. The method of claim 4, further comprising:

capturing, via an acceleration sensor, an acceleration parameter of the drive unit simultaneously during the capturing the first position parameter and the capturing the second position parameter;

determining a motorized input of force of the drive unit based on the acceleration parameter; and correcting the adjusting force based on the motorized input of force.

6. The method of claim 2, further comprising:

capturing, via an acceleration sensor, an acceleration parameter of the drive unit simultaneously during the capturing the first position parameter and the capturing the second position parameter;

determining a motorized input of force of the drive unit based on the acceleration parameter; and correcting the adjusting force based on the motorized input of force.

7. The method of claim 6, wherein the correcting corrects the adjusting force by subtracting of the motorized input of force.

8. The method of claim 2, wherein the capturing the first position and the capturing the second position occurs simultaneously.

9. The method of claim 1, wherein the capturing the first position and the capturing the second position occurs simultaneously.

10. The method of claim 1, wherein the generating the control signal includes, generating, based on the position spacing, a torque specification for the drive unit for direction-dependent friction compensation.

11. A system for controlling a motion of a component of a medical installation, the system comprising:

a first position sensor on the component, the first position sensor configured to capture a first position parameter;

a second position sensor on the component, the second position sensor configured to capture a second position parameter; and a control unit configured to, determine a position spacing for the first position sensor and the second position sensor a plurality of times with a time interval based on the first position parameter and the second position parameter by subtracting a previously defined offset specific to the component and representing a non-elastic deformability of the component if a sign of the position spacing changes between two iterations of the position spacing being determined, and generate a control signal for a drive unit of the component based on the determined position spacing, wherein the component is movable and elastic, and an elastic deformation of the component is caused by an operating force introduced manually by a user.

12. The system of claim 11, wherein the first position sensor and the second position sensor are on the component such that the first position sensor and the second position sensor have a maximum spacing at rest to one another along a spatial axis.

13. The system of claim 12, comprising:

pairs of the first position sensor and the second position sensor for each spatial axis, wherein the control unit is configured to generate a position spacing for the position sensor pairs of each spatial axis and a respective control signal for the drive unit of each spatial axis based on the respective position spacing.

14. The system of claim 13, wherein the first position sensor is a rotary encoder of the drive unit.

15. The system of claim 11, comprising:

pairs of the first position sensor and the second position sensor for each spatial axis, wherein the control unit is configured to generate a position spacing for the position sensor pairs of each spatial axis and a respective control signal for the drive unit of each spatial axis based on the respective position spacing.

16. The system of claim 11, wherein the first position sensor is a rotary encoder of the drive unit.

17. A medical installation comprising:

the system of claim 11;

the component, the component being movable; and the drive unit.

18. The medical installation of claim 17, wherein the component is a stand to support an imaging unit or a patient table.

* * * * *